United States Patent

Wade et al.

[11] 4,170,651
[45] Oct. 9, 1979

[54] 2-SUSTITUTED-1H-BENZ-[de]-ISOQUINO-LINE-1,3(2H)-DIONES

[75] Inventors: Peter C. Wade, Pennington, N.J.; Berthold R. Vogt, Yardley, Pa.

[73] Assignee: E. R. Squibb & Sons, Inc., Princeton, N.J.

[21] Appl. No.: 923,882

[22] Filed: Jul. 12, 1978

Related U.S. Application Data

[62] Division of Ser. No. 812,886, Jul. 5, 1977, Pat. No. 4,115,555, which is a division of Ser. No. 727,836, Sep. 9, 1976, Pat. No. 4,051,246.

[51] Int. Cl.² .................. C07D 217/24; A61K 31/47
[52] U.S. Cl. ................................ 424/258; 546/98; 546/99
[58] Field of Search .......... 260/281 A, 281 S, 281 N; 424/258; 546/98, 99

[56] References Cited

U.S. PATENT DOCUMENTS

| | | | |
|---|---|---|---|
| 3,247,208 | 4/1966 | Schenker et al. | 260/281 |
| 3,876,642 | 4/1975 | Dorlars et al. | 260/281 |
| 3,925,227 | 1/1976 | Wade et al. | 260/281 S |
| 3,939,093 | 2/1976 | Papenfuhs | 260/281 |
| 3,940,397 | 2/1976 | Wade et al. | 260/268 TR |
| 3,940,398 | 2/1976 | Wade et al. | 424/250 |
| 3,947,452 | 3/1976 | Wade et al. | 260/281 NA |
| 3,959,286 | 5/1976 | Wade et al. | 260/281 NH |
| 3,996,362 | 12/1976 | Wade et al. | 424/258 |
| 3,996,363 | 12/1976 | Wade et al. | 424/258 |
| 4,006,238 | 2/1977 | Wade | 424/258 |
| 4,062,953 | 12/1977 | Wade et al. | 424/232 |
| 4,070,465 | 12/1978 | Wade et al. | 424/250 |

*Primary Examiner*—Mark L. Berch
*Attorney, Agent, or Firm*—Lawrence S. Levinson; Merle J. Smith; Stephen B. Davis

[57] ABSTRACT

Compounds of the following formula

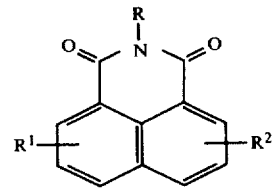

wherein $R^1$ and $R^2$ are independently selected from hydrogen, halogen, lower alkyl, lower alkoxy, lower alkylthio, nitro, cyano, and trifluoromethyl, and R is selected from a triacetyl substituted pentose, pentose, a tetraacetyl substituted hexose, hexose, a hydroxy substituted cycloalkyl of 5 to 7 carbons,

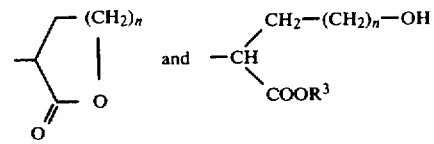

wherein n is 1 or 2 and $R^3$ is hydrogen, an alkali metal or alkaline earth metal ion; are disclosed. These compounds possess useful anti-inflammatory activity.

6 Claims, No Drawings

2-SUBSTITUTED-1H-BENZ-[de]-ISOQUINOLINE-1,3(2H)-DIONES

This application is a division of Ser. No. 812,886 filed on July 5, 1977, now U.S. Pat. No. 4,115,555 which in turn was a division of Ser. No. 727,836 filed on Sept. 9, 1976, now U.S. Pat. No. 4,051,246.

BACKGROUND OF THE INVENTION

Various 2-[(substituted heterocyclic)alkyl]-1H-benz-[de]isoquinoline-1,3(2H)-diones having central nervous system and anti-inflammatory activity are disclosed by Wade et al. in U.S. Pat. Nos. 3,935,227; 3,940,397; 3,940,398; 3,947,452; and 3,959,286. Also, Schenker in U.S. Pat. No. 3,247,208 disclose that 1H-benz-[de]isoquinoline-1,3(2H)-diones having a (1-substituted-4-piperidinyl) group in the 2-position possess anesthetic properties.

SUMMARY OF THE INVENTION

This invention is directed to new compounds of the formula

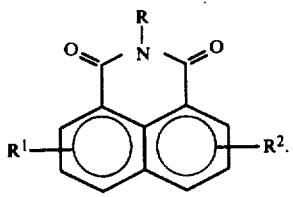

(I)

The symbols have the following meaning in formula I and throughout this specification.

$R^1$ and $R^2$ are independently selected from hydrogen, halogen, lower alkyl, lower alkoxy, lower alkylthio, nitro, amino, trifluoromethyl, and cyano.

R is selected from triacetyl substituted pentose, pentose, tetraacetyl substituted hexose, hexose, hydroxy substituted cycloalkyl of 5 to 7 carbons,

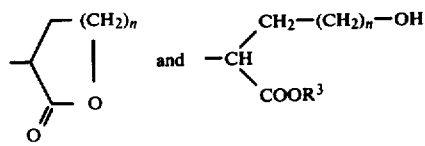

wherein n is 1 or 2 and $R^3$ is hydrogen, an alkali metal or alkaline earth metal ion.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The lower alkylthio group include such lower alkyl groups attached to a sulfur, e.g., methylthio, ethylthio, etc.

Halogen is intended to include chlorine, bromine, fluorine, and iodine, with chlorine, bromine and fluorine being preferred and chlorine being most preferred.

The salt forming ions represented by $R^3$ may be an alkali metal ion such as sodium or potassium or an alkaline earth metal ion such as calcium or magnesium.

The term "pentose" is meant to include D-ribose, D-arabinose, D-xylose, and D-lyxose and the term "hexose" is meant to include D-glucose, D-allose, D-gulose, D-galactose, D-altrose, D-mannose, D-idose and D-talose.

Preferred among the compounds of formula I are those of the formula

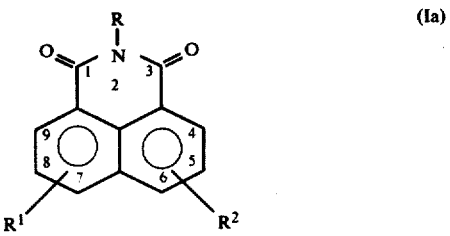

(Ia)

wherein $R^1$ and $R^2$ are independently selected from hydrogen, Cl, Br, F, methyl, and methoxy and are located at the 7- or 8-position and 5- or 6-position respectively.

Most preferred are the compounds of formula Ia wherein $R^1$ and $R^2$ are both hydrogen and R is tetraacetyl substituted glucose, glucose, 4-hydroxycyclohexyl,

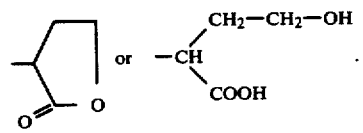

The new compounds of this invention wherein R is a triacetyl substituted pentose or tetraacetyl substituted hexose are prepared by reacting the sodium salt of a substituted naphthalimide (prepared by reacting the naphthalimide with sodium hydroxide) of the formula

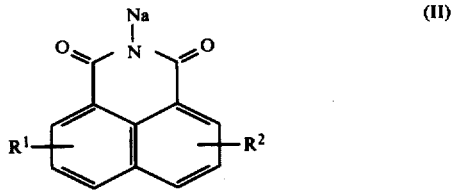

(II)

with a halo (Cl or Br) substituted pentose triacetate or a halo substituted hexose tetraacetate in an inert organic solvent such as dimethylformamide at about room temperature.

Acid hydrolysis of this resulting triacetyl pentose or tetraacetyl hexose yields the corresponding pentose or hexose compound of formula I.

The compounds of formula I wherein R is hydroxy substituted cycloalkyl of 5 to 7 carbons are prepared by reacting the substituted naphthalic anhydride of formula

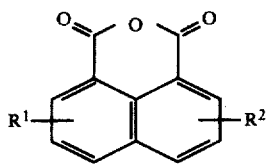

with a disubstituted cycloalkyl of 5 to 7 carbons wherein the substituents are on different carbon atoms and one is a hydroxy and other is an amino group. The reaction is performed by heating at reflux temperature for several hours in an organic solvent such as butanol. The disubstituted cycloalkyl employed in this reaction can be in either the cis or trans configuration and such configuration will be retained in the final product.

The compounds of formula I wherein R is

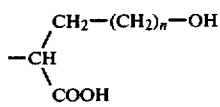

are prepared by reacting the substituted naphthalic anhydride of formula III with a compound of formula

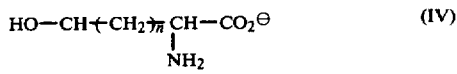

by heating for several hours at reflux temperature in an inert solvent. Treatment of the resulting acid with a source of alkali metal or alkaline earth metal ion such as sodium hydroxide or calcium hydroxide yields the compounds of formula I wherein $R^3$ is an alkali metal or alkaline earth metal ion.

The reactant of formula IV is prepared by treating a hydrohalide salt of the formula

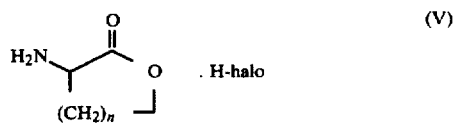

wherein halo is Br or Cl with two equivalents of a base such as sodium hydroxide.

The compounds of formula I wherein R is

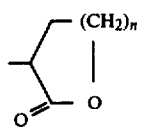

are prepared by reacting the sodium salt of a substituted naphthalimide of formula II with a compound of formula

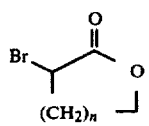

by heating in an organic solvent such as dimethylformamide at about 80° to about 100° C. for about an hour.

The reactants of formulas II to VI as well as the halo substituted pentose triacetate, halo substituted hexose tetraacetate, and amino substituted cycloalkanol are known in the art or are prepared by methods known in the art.

The compounds of formula I are useful in treating inflammation in mammalian species, e.g., rats, dogs, cats, monkeys, etc. Joint tenderness and stiffness (in conditions such as rheumatoid arthritis) are relieved by the above described compounds.

The compound or mixture of compounds of formula I can be used as antiinflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts ranging from about 1 mg./kg./day to about 30 mg./kg./day, preferably from about 3 mg./kg./day to about 15 mg./kg./day. A preferred unit dose for use in treating a 70 kg. mammal would contain from 210 mg. to about 1,050 mg. of active ingredient.

The following examples are illustrative of the invention and represent preferred embodiments. Other modifications may be readily produced by suitable variations of the reactants. All temperatures are in the centigrade scale.

EXAMPLE 1 trans-(4-Hydroxycyclohexyl)-1H-benz[de]isoquinoline-1,3-(2H)-dione 7.5 g. (0.0378 moles) of naphthalic anhydride and 4.35 g. (0.0378 moles) of trans-4-aminocyclohexanol are refluxed in 250 ml. of n-butanol for two hours. After standing overnight at room temperature, crude product crystallizes and is removed from the reaction mixture by filtration. This material is dissolved in chloroform. The chloroform solution is washed with 10% sodium hydroxide, then water, and is finally evaporated. The residue is recrystallized from ethanol to yield 4.78 g. of trans-4-(hydroxycyclohexyl)-1H-benz[de]isoquinoline-1,3(2H)-dione; m.p. 245°-246°.

EXAMPLE 2 cis-(4-Hydroxycyclohexyl)-1H-benz[de]isoquinoline-1,3(2H)-dione 6.03 g. (0.0304 moles) of naphthalic anhydride and 3.5 g. (0.0304 moles) of cis-4-aminocyclohexanol are refluxed in 200 ml. of n-butanol for 3.5 hours. Employing the same crystallization procedure as in example 1, one obtains 5.1 g. of cis-(4-hydroxycyclohexyl)-1H-benz[de]isoquinoline-1,3(2H)-dione; m.p. 240°-242°.

EXAMPLES 3-16

Following the procedure of example 1 or 2 but employing an equivalent amount of the following aminocycloalkanols:
trans-3-aminocyclopentanol;
cis-3-aminocyclopentanol;
trans-2-aminocyclopentanol;
cis-2-aminocyclopentanol;
trans-3-aminocyclohexanol;
cis-3-aminocyclohexanol;
trans-2-aminocyclohexanol;
cis-2-aminocyclohexanol;
trans-2-aminocycloheptanol;
cis-2-aminocycloheptanol;

trans-3-aminocycloheptanol;
cis-3-aminocycloheptanol;
trans-4-aminocycloheptanol; and
cis-4-aminocycloheptanol;
one obtains the following products:
trans-(3-hydroxycyclopentanol)-1H-benz[de]isoquinoline-1,3(2H)-dione;
cis-(3-hydroxycyclopentanol)-1H-benz[de]isoquinoline-1,3(2H)-dione;
trans-(2-hydroxycyclopentanol)-1H-benz[de]isoquinoline-1,3(2H)-dione;
cis-(2-hydroxycyclopentanol)-1H-benz[de]isoquinoline-1,3(2H)-dione;
trans-(3-hydroxycyclohexanol)-1H-benz[de]isoquinoline-1,3(2H)-dione;
cis-(3-hydroxycyclohexanol)-1H-benz[de]isoquinoline-1,3(2H)-dione;
trans-(2-hydroxycyclohexanol)-1H-benz[de]isoquinoline-1,3(2H)-dione;
cis-(2-hydroxycyclohexanol)-1H-benz[de]isoquinoline-1,3(2H)-dione;
trans-(2-hydroxycycloheptanol)-1H-benz[de]isoquinoline-1,3(2H)-dione;
cis-(2-hydroxycycloheptanol)-1H-benz[de]isoquinoline-1,3(2H)-dione;
trans-(3-hydroxycycloheptanol)-1H-benz[de]isoquinoline-1,3(2H)-dione;
cis-(3-hydroxycycloheptanol)-1H-benz[de]isoquinoline-1,3(2H)-dione;
trans-(4-hydroxycycloheptanol)-1H-benz[de]isoquinoline-1,3(2H)-dione; and
cis-(4-hydroxycycloheptanol)-1H-benz[de]isoquinoline-1,3(2H)-dione; respectively.

EXAMPLES 17–42

Following the procedure of example 1 but employing the substituted naphthalic anhydride shown below in Col. I one obtains the product shown in Col. II.

| Ex. | $X^1$ | $X^2$ | $X^3$ | $X^4$ | $X^5$ | $X^6$ |
|---|---|---|---|---|---|---|
| 17 | H | H | Br | H | H | H |
| 18 | H | Cl | H | H | H | H |
| 19 | H | Br | H | H | H | H |
| 20 | H | F | H | H | H | H |
| 21 | H | I | H | H | H | H |
| 22 | H | Cl | H | H | Cl | H |
| 23 | Br | H | H | H | H | H |
| 24 | H | H | Cl | Cl | H | H |
| 25 | H | H | $CH_3$ | H | H | H |
| 26 | H | H | $C_2H_5$ | H | H | H |
| 27 | H | H | $i-C_3H_7$ | H | H | H |
| 28 | H | H | $CH_3$ | $CH_3$ | H | H |
| 29 | H | H | $OCH_3$ | H | H | H |
| 30 | H | H | $OC_2H_5$ | H | H | H |
| 31 | H | H | $OC_3H_7$ | H | H | H |
| 32 | H | H | $OCH_3$ | $OCH_3$ | H | H |
| 33 | H | $NO_2$ | H | H | H | H |
| 34 | H | H | $NO_2$ | H | H | H |
| 35 | H | $CF_3$ | H | H | H | H |
| 36 | H | H | $CF_3$ | H | H | H |
| 37 | H | CN | H | H | H | H |
| 38 | H | H | CN | H | H | H |
| 39 | H | H | $NH_2$ | H | H | H |
| 40 | H | $NH_2$ | H | H | H | H |
| 41 | H | $SC_3H_7$ | H | H | H | H |
| 42 | H | H | $SCH_3$ | H | H | H |

Similarly, by employing the substituted naphthalic anhydride of examples 17 to 42 within the procedure of examples 2 to 16 other compounds within the scope of the invention are obtained.

EXAMPLE 43

1,3-Dihydro-α-(2-hydroxyethyl)-1,3-dioxo-2H-benz[de]isoquinoline-2-acetic acid 16.5 g. (0.0904 moles) of 3-amino-4,5-dihydro-2(3H)-furanone hydrobromide is dissolved in 181 ml. of 1N sodium hydroxide and refluxed for 15 minutes. 17.91 g. (0.0904 moles) of naphthalic anhydride is added and the mixture is refluxed overnight. The reaction mixture is filtered to remove a small amount of insoluble material. The reaction mixture is then acidified with concentrated HCl to precipitate crude product which is removed by filtration. This material is washed with water and recrystallized from 800 ml. of dioxane to yield 14.95 g. of 1,3-dihydro-α-(2-hydroxyethyl)-1,3-dioxo-2H-benz[de]isoquinoline-2-acetic acid; preliminary melting at approximately 240°, resolidifies and melts at 295°–297°.

An aqueous suspension of this acid is treated with sodium hydroxide or calcium hydroxide and lyophilized to yield the corresponding sodium or calcium salt.

EXAMPLE 44

1,3-Dihydro-α-(3-hydroxypropyl)-1,3-dioxo-2H-benz[de]isoquinoline-2-acetic acid

Following the procedure of example 43 but substituting an equivalent amount of 3-aminotetrahydro-2H-pyran-2-one for the furanone one obtains 1,3-dihydro-α-(3-hydroxypropyl)-1,3-dioxo-2H-benz[de]isoquinoline-2-acetic acid.

Similarly, by employing the substituted naphthalic anhydrides shown in Col. I of examples 17 to 42 within the procedure of example 43 or 44 other compounds within the scope of the invention are obtained.

EXAMPLE 45

2-(Tetrahydro-2-oxo-3-furanyl)-1H-benz[de]isoquinoline-1,3(2H)-dione 10 g. (0.0507 moles) of naphthalimide is dissolved in 200 ml. of hot (90°) dimethylformamide with stirring. 2.06 g. (0.0507 moles) of sodium hydroxide dissolved in 50 ml. of hot ethanol is added causing the naphthalimide sodium salt to precipitate. The sodium salt is filtered off at room temperature, washed with ethanol, and is taken up in 200 ml. of hot (90°) dimethylformamide. 8.37 g. (0.0507 moles) of 3-bromo-4,5-dihydro-2(3H)-furanone in a small amount of dimethylformamide is added to the sodium salt solution. This mixture is heated at from 80° to 100° for an hour and crude organic material is precipitated by the addition of 500 ml. of water. This material is filtered off, washed with water and recrystallized from 600 ml. of dioxane. Additional recrystallization from 25 ml. of dimethylformamide25 ml. of isopropyl alcohol yields 3.1 g. of 2-(tetrahydro-2-oxo-3-furanyl)-1H-benz[de]isoquinoline-1,3(2H)-dione; m.p. 310°–312°.

EXAMPLE 46

2-(Tetrahydro-2-oxo-2H-pyran-3-yl)-1H-benz[de]isoquinoline-1,3(2H)-dione

Following the procedure of example 45 but substituting an equivalent amount of 3-bromotetrahydro-2H-pyran-2-one for the furanone one obtains 2-(tetrahydro-2-oxo-2H-pyran-3-yl)-1H-benz[de]isoquinoline-1,3(2H)-dione.

EXAMPLES 47–72

Following the procedure of example 45 but employing the substituted naphthalimide shown below in Col. I one obtains the final products shown in Col. II.

| Ex. | $X^1$ | $X^2$ | $X^3$ | $X^4$ | $X^5$ | $X^6$ |
|---|---|---|---|---|---|---|
| 47 | H | H | Br | H | H | H |
| 48 | H | Cl | H | H | H | H |
| 49 | H | Br | H | H | H | H |
| 50 | H | F | H | H | H | H |
| 51 | H | I | H | H | H | H |
| 52 | H | Cl | H | H | Cl | H |
| 53 | Br | H | H | H | H | H |
| 54 | H | H | Cl | Cl | H | H |
| 55 | H | H | $CH_3$ | H | H | H |
| 56 | H | H | $C_2H_5$ | H | H | H |
| 57 | H | H | $i$-$C_3H_7$ | H | H | H |
| 58 | H | H | $CH_3$ | $CH_3$ | H | H |
| 59 | H | H | $OCH_3$ | H | H | H |
| 60 | H | H | $OC_2H_5$ | H | H | H |
| 61 | H | H | $OC_3H_7$ | H | H | H |
| 62 | H | H | $OCH_3$ | $OCH_3$ | H | H |
| 63 | H | $NO_2$ | H | H | H | H |
| 64 | H | H | $NO_2$ | H | H | H |
| 65 | H | $CF_3$ | H | H | H | H |
| 66 | H | H | $CF_3$ | H | H | H |
| 67 | H | CN | H | H | H | H |
| 68 | H | H | CN | H | H | H |
| 69 | H | H | $NH_2$ | H | H | H |
| 70 | H | $NH_2$ | H | H | H | H |
| 71 | H | $SC_3H_7$ | H | H | H | H |
| 72 | H | H | $SCH_3$ | H | H | H |

Similarly, by employing the substituted naphthalimides of Col. I within the procedure of example 46 other compounds within the scope of the invention are obtained.

EXAMPLE 73

2-$\beta$-D-Glucosyl-1H-benz[de]isoquinoline-1,3(2H)-dione, tetraacetate ester 15 g. (0.12 moles) of naphthalimide is dissolved in 300 ml. of dimethylformamide at 100°. 5.71 g. (0.12 moles) of sodium hydroxide dissolved in 30 ml. of methanol is added dropwise over 5 minutes. The naphthalimide sodium salt precipitates and is stirred as a suspension at 100° for 15 minutes, cooled to room temperature, filtered off, washed with dimethylformamide and toluene, and dried at 100° under vacuum.

25 g. (0.0547 moles) of α-D-acetobromglucose is added to a stirred suspension of the naphthalimide sodium salt in 200 ml. of dimethylformamide at room temperature. The naphthalimide sodium salt dissolves after 15 minutes. The solution is stirred for one hour and poured into 400 ml. of water to precipitate a crude product. This product is filtered off, washed with water, ethanol, and ether. The slightly colored white solid material is taken up in 200 ml. of chloroform, filtered, and the filtrate evaporated. Recrystallization from 350 ml. of ethanol yields 11.15 g. of 2-$\beta$-D-glucosyl-1H-benz[de]isoquinoline-1,3(2H)-dione, tetraacetate ester; m.p. 195°–196°.

EXAMPLES 74–82

Following the procedure of example 73 but substituting for the α-D-acetobromglucose one of the following:
D-bromoarabinose triacetate;
D-chloroxylose triacetate;
D-bromolyxose triacetate;
D-chloroallose tetraacetate;
D-bromogalactose tetraacetate;
D-chloroaltrose tetraacetate;
D-bromomannose tetraacetate;
D-chloroidose tetraacetate; and
D-bromotalose tetraacetate
one obtains the following products:

2-D-arabinosyl-1H-benz[de]isoquinoline-1,3(2H)-dione, triacetate ester;

2-D-xylosyl-1H-benz[de]isoquinoline-1,3(2H)-dione, triacetate ester;

2-D-lyxosyl-1H-benz[de]isoquinoline-1,3(2H)-dione, triacetate ester;

2-D-allosyl-1H-benz[de]isoquinoline-1,3(2H)-dione, tetraacetate ester;

2-D-galactosyl-1H-benz[de]isoquinoline-1,3(2H)-dione, tetraacetate ester;

2-D-altrosyl-1H-benz[de]isoquinoline-1,3(2H)-dione, tetraacetate ester;

2-D-mannosyl-1H-benz[de]isoquinoline-1,3(2H)-dione, tetraacetate ester;

2-D-idosyl-1H-benz[de]isoquinoline-1,3(2H)-dione, tetraacetate ester; and

2-D-talosyl-1H-benz[de]isoquinoline-1,3(2H)-dione, tetraacetate ester; respectively.

Similarly, by employing the substituted naphthalimides shown in Col. I of examples 47 to 72 within the procedure of examples 73 to 82 other compounds within the scope of the invention are obtained.

EXAMPLE 83

2-β-D-Glucosyl-1H-benz[de]isoquinoline-1,3(2H)-dione 7.15 g. (0.0136 moles) of 2-β-D-glucosyl-1H-benz[de]isoquinoline-1,3(2H)-dione, tetraacetate ester from example 73 is dissolved in 250 ml. of hot ethanol and 10 ml. of 5N ethanolic HCl is added. Crystallization occurs upon allowing the solution to stand for two days. The crystals are removed by filtration and recrystallized from dimethylformamide/ethanol to yield 3.45 g. of 2-β-D-glucosyl-1H-benz[de]isoquinoline-1,3(2H)-dione; m.p. 285°–286°.

Similarly, by employing the procedure of example 83 on the final products of examples 74 to 82 other compounds within the scope of the invention are obtained.

What is claimed is:

1. A compound of the formula:

wherein $R^1$ and $R^2$ are independently selected from the group consisting of hydrogen, lower alkyl, lower alkoxy, halogen, lower alkylthio, nitro, cyano, and trifluoromethyl; and R is cycloalkanol of 5 to 7 carbons.

2. The compound of claim 1 having the formula:

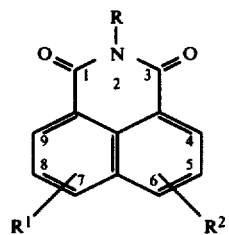

wherein $R^1$ and $R^2$ are independently selected from the group consisting of hydrogen, Cl, Br, F, methyl and methoxy and are located at the 7- or 8-position and 5- or 6-position respectively.

3. The compound of claim 2 wherein R is cyclohexanol and $R^1$ and $R^2$ are both hydrogen.

4. The compound of claim 3, trans-(4-hydroxycyclohexyl)-1H-benz[de]isoquinoline-1,3(2H)-dione.

5. The compound of claim 3, cis-(4-hydroxycyclohexyl)-1H-benz[de]isoquinoline-1,3(2H)-dione.

6. The method of treating inflammation in a mammalian specie comprising administering a composition containing a pharmaceutically acceptable carrier and as the active ingredient from about 1 mg./kg. to about 30 mg./kg. of a compound or mixture of compounds of claim 1.

* * * * *